United States Patent [19]

Yoshisato et al.

[11] Patent Number: 4,642,169
[45] Date of Patent: Feb. 10, 1987

[54] CONTINUOUS ROTATING ELECTROPHORESIS COLUMN AND PROCESS OF USING

[75] Inventors: Randall A. Yoshisato; Ravindra Datta; Gregory R. Carmichael, all of Iowa City, Iowa

[73] Assignee: University of Iowa Research Foundation, Iowa City, Iowa

[21] Appl. No.: 833,654

[22] Filed: Feb. 21, 1986

Related U.S. Application Data

[63] Continuation-in-part of Ser. No. 636,612, Aug. 1, 1984.

[51] Int. Cl.[4] .............................................. G01N 27/26
[52] U.S. Cl. .............................. 204/180.1; 204/299 R
[58] Field of Search ............... 204/180.1, 182.6, 182.8, 204/299 R, 300 R

[56] References Cited

U.S. PATENT DOCUMENTS

| | | | |
|---|---|---|---|
| 2,992,979 | 7/1961 | Magnuson et al. | 204/300 R |
| 3,556,967 | 1/1971 | Anderson | 204/299 R |
| 3,616,453 | 11/1971 | Phillpet | 204/299 R |
| 3,704,217 | 11/1972 | Nerenberg | 204/299 R |
| 3,814,678 | 6/1974 | Fletcher | 204/180 R |
| 3,844,926 | 10/1974 | Smyth et al. | 204/299 R |
| 4,018,662 | 4/1977 | Ruhenstroth-Bauer et al. | 204/299 R |
| 4,040,940 | 8/1977 | Bier | 204/299 R |
| 4,141,809 | 2/1979 | Aitchison et al. | 204/180 R |
| 4,182,678 | 1/1980 | Ito | 210/198 C |
| 4,315,812 | 2/1982 | Karlson | 204/299 R |
| 4,358,358 | 11/1982 | Rhodes | 204/299 R |
| 4,375,401 | 3/1983 | Catsimpoolas | 204/299 R |
| 4,432,849 | 2/1984 | Saito | 204/180 R |
| 4,440,638 | 4/1984 | Judy et al. | 204/302 |

OTHER PUBLICATIONS

McDonald et al., "Centrifugal Force in Paper Chrometography and Electrophoresis", Analytical Chemistry, vol. 31, No. 5, May '59, pp. 825–829.
Vermeulen, T., et al., "Design Theory and Separations in Preparative-Scale Continuous-Flow Annular-Bed Electrophoresis," *Ing. Eng. Chem. Process Des. Develop.*, 10:91–102 (1971).
Fox, J. B., et al., "Continuous Chromatography Apparatus, Part I, Construction," *J. Chromatog.*, 43:48–54 (1969).
Fox, J. B., "Continuous Chromatography Apparatus, Part II, Operation," *J. Chromatog.*, 43:55–60 (1969).
Nicholas, R. A. and Fox, J. B., "Continuous Chromatography Apparatus, Part III, Application," *J. Chromatog.*, 43:61–65 (1969).
Begovich, J. M., "Multicomponent Separations Using a Continuous Annular Chromatography," Ph.D. Dissertation, University of tennesee, Knoxville, TN (1982).
Begovich, J. M. and Sisson, W. G., "A Rotating Annular Chromatograph for Continuous Separations," submitted to *AIChE J*.
*Chemical Engineering*, vol. 90, No. 8, pp. 10–11 (1983).
"Gene-Splicing Methods Move From Lab to Plant", *Chemical Engineering*, vol. 90, No. 12, p. 25 (1983).

*Primary Examiner*—Terryence Chapman
*Attorney, Agent, or Firm*—Henderson & Sturm

[57] ABSTRACT

A continuous rotating annular electrophoresis column for the separation of chemical mixtures. The principle of separation is similar to the conventional electrophoresis; however, it is different in that the electric field is applied in the axial direction and the column is rotated. By rotating the column, the product path appears as helical bands, each with a characteristic, stationary exit point at some angular coordinate at the bottom of the column. By applying the electric field axially, the bed thickness can be kept thin for effective heat transfer and temperature control. The apparatus can be used in the separations of biochemically active compounds, or to separate, based on the principal of charge, any chemical mixture. The column can also be packed with chromographic materials and thus operate as a electrochromographic separator.

16 Claims, 2 Drawing Figures

CONTINUOUS ROTATING ELECTROPHORESIS COLUMN AND PROCESS OF USING

This is a continuation-in-part of co-pending application Ser. No. 636,612 filed on Aug. 1, 1984.

TECHNICAL FIELD

This invention relates to separation apparatus, and more particularly to electrophoretic separation apparatus suitable for the continuous separation and purification of mixtures of products from industrial scale biological processes.

BACKGROUND ART

The recent advances in genetic engineering and biotechnology have placed the chemical process industry at the doorstep of a new era of products never before commercially available. The production of human insulin on a commercial basis has already begun and other pharmaceuticals are certain to follow as processes are developed for producing these highly complex molecules which may have a profound impact on our ability to treat disease and metabolic abnormalities. Pesticides, fertilizers and fine chemicals will also be likely candidates for new biotechnology applications.

As the new biotechnological processes are developed and scaled-up to production levels, the separation and purification of products will be a critical factor in determining the technical feasibility as well as the economic success of the process. Indeed, the second largest cost associated with producing products from biological processes is the cost of the product separation and purification.

Distillation and extraction are the most widely used methods in the petrochemical industry; however, these methods are generally unsuitable for bioseparations. Many biochemically active compounds are active only over specific ranges of temperature, pH, and ionic strength. The molecule may also be affected by interaction with the solvent. These conformational changes are not necessarily reversible so great care must be taken to ensure mild operating conditions and thus avoid degradation of the valuable product during the recovery phase. Furthermore, fermentation broths are typically quite dilute compared to other chemical process streams, and contain a complex mixture of substances some of which are closely related to the desired product.

Due to these rather severe limitations, membrane processes, ultra-centrifugation, differential precipitation, electrophoresis and chromatography are the techniques used most often in bench scale procedures. These procedures are usually performed batchwise and have very small product throughputs—milligram quantities are not uncommon as an upper limit.

Electrophoresis and chromatography are the two most useful techniques to modern chemical analysis. They have the highest resolution and can be quite highly specific when used in conjunction with affinity or immunochemical techniques. Electrophoresis is a particularly attractive technique since it has high resolution capability and would be most useful in the final purification of products. Furthermore, since it separates principally on the basis of charge rather than size, it is well-suited for the separation of similarly sized charged molecules from one another as well as from uncharged molecules.

The problems involved in the implementation of an electrophoresis process capable of industrial-scale use are not in the physical separation of products, but rather in the practical engineering design of the electrophoretic device. Such a device must provide for (1) the continuous supply of both elutant and feed to the bed, (2) the continuous removal of products from the bed, (3) the efficient removal of heat from the bed to limit the bed temperature rise, (4) large throughput, and (5) a large number of purified product fractions. A search of the prior art revealed the following:

Vermeulen and colleagues ("Design Theory and Separations in Preparative-Scale Continuous-Flow Annular-Bed Electrophoresis", *Ind. Eng. Chem. Process Des. Develop.*, 10:91–102 (1971)) have developed a continuous flow electrophoretic separator. It separates product in the radial direction and is limited in the number of products. Furthermore, the heating which takes place causes a substantial temperature rise.

Nerenburg (U.S. Pat. No. 3,704,217) describes a batch or non-continuous electrophoretic separation device whereby a batch sample is introduced in a packed column and the current is turned on to separate the sample into various components. The current is then turned off and the various products are found to be distributed along the length of the bed. A series of ports along the bed provide a means for washing out a given product at an intermediate location and eliminating the need for the product to traverse the entire length of the column.

Anderson (U.S. Pat. No. 3,556,967) describes a batch or non-continuous electrophoretic separation device whereby a density gradient is established in a rapidly spinning centrifuge rotor. The batch sample is introduced into this density gradient and the current is turned on. Separation takes place and mixing due to thermal heating is minimized as a result of the density gradient coupled with the centrifugal field. After the separation is complete the current is turned off. The density gradient and the separated products are then pumped out.

Bier (U.S. Pat. No. 4,040,940) describes a batch or non-continuous electrophoretic separation device which employs a rotational seal fraction collector. The actual separation device uses the method of rotationally stabilized flow in the annulus between horizontal concentric cylinders. The operation of this device requires that the annulus first be filled with elutant. The batch sample is introduced into the elutant stream. At this time, the rotation is started and the current turned on. As the separation takes place under the influence of the electric field, the product bands move toward the collector by the flow of elutant. At the collector, a small jet perpendicular to the flow forces the product out.

Fox, et al., ("Continuous Chromatography Apparatus, Part I, Construction," *J. Chromatog.*, 43: 48–54 (1969); "Continuous Chromatography Apparatus, Part II, Operation" 43: 55–60 (1960); and "Continuous Chromatography Apparatus, Part III, Application," 43: 61–65 (1960)) and Begovich, et al., ("Multicomponent Separations Using a Continuous Annular Chromatograph," Ph.D. Dissertation, University of Tennessee, Knoxville, TN. (1982); "A Rotating Annular Chromatograph for Continuous Separations," Submitted to *AIChE J.*) have demonstrated the use of a slowly rotating annular bed of sorbent material to effect continuous chromatographic multicomponent separations. The rotation of the bed causes the separated components to appear as helical bands, each of which has a characteristic stationary exit point at some angular coordinate at the bottom of the column.

Note that in electrophoresis, actual separation only takes place while the electric current is on. Furthermore, a continuous process is one whereby the elutant and sample are introduced continuously into the device. Thus, the need for a continuous electrophoretic separation device which has a continual supply of elutant, sample or feed and electric current to maintain separation in the device at all times is required. Previous devices are not fully continuous and therefore, require that the device be operated in a cyclical fashion. At some point in the operation, the device must cease performing its separation function in order for it to be returned to some initial condition in order to receive a new sample for separation.

Although continuous electrophoresis is industrially attractive and feasible, for the full scale commercialization of recent advances in biotechnology, separation processes must be developed and refined to allow continuous operation and higher throughputs while still observing the restrictions mentioned previously to maintain bioactivity of the product.

Those concerned with these and other problems recognize the need for an improved apparatus for the separation of binary and multi-component mixtures of products from biological processes.

DISCLOSURE OF THE INVENTION

The present invention provides a truly continuous rotating annular electrophoresis column for the separation of chemical mixtures. The principle of separation is similar to the conventional electrophoresis; however, it is different in that the electric field is applied in the axial direction and the column is rotated. By rotating the column, the product path appears as helical bands, each with a characteristic, stationary exit point at some angular coordinate at the bottom of the column. By applying the electric field axially, the bed thickness can be kept thin for effective heat transfer and temperature control. The apparatus can be used in the separations of biochemically active compounds, or to separate, based on the principal of charge, any chemical mixture. The column can also be packed with chromographic materials and thus operate as a electrochromographic separator.

In the apparatus of the present invention, the electrical field is applied in the axial rather than the radial direction. Application of the electrical field in an axial direction changes the product path from the radial direction to the angular direction. Thus, the bed thickness can be kept thin for effective heat transfer and temperature control while still having sufficient path length for maximum product resolution.

The separation is truly continuous since it allows for the continuous supply of elutant and feed or sample to enter the device and the continuous taking of separated product from the bottom of the column. Furthermore, the device allows for the continuous supply of electric current so that actual separation is performed at all times. This eliminates the need for turning on and off the electric current during operation in order to remove product. Also, since sample is fed continuously rather than in a batch sample as by others, there is no lost time required to restore the device to its initial state for additional batch sample introduction.

An object of the present invention is the provision of an improved separation apparatus.

Another object is to provide a separation apparatus having high resolution capability while providing for product stability.

A further object of the invention is the provision of a continuous separation apparatus wherein the throughput can be adjusted to be compatible with a variety of industrial applications.

Still another object is to provide a rotating annular electrophoresis column wherein the rotation allows the material migration path to be lengthened without increasing the annular bed length and stabilizes the laminar flow of the carrier solution.

A still further object of the present invention is the provision of a rotating annular electrophoresis column having a thin annulus width to improve heat transfer and optimize temperature control.

A still further object of the present invention is to provide a continuous supply of elutant.

A still further object is to provide a continuous supply of feed or sample to be separated.

A still further object is to provide a continuous supply of electric current.

A still further object is to provide the means for continuous separation to occur in the device.

A still further object is to eliminate the need to return an electrophoretic device to its initial state in order to commence a new separation cycle.

Yet another object is to provide a continuous rotating annular electrophoresis column having stationary feed points and a plurality of stationary product collection points.

A further object of the present invention is the provision of a continuous rotating annular electrophoresis column wherein the annular column is adapted to incorporate chromatographic packing, thus combining the separation advantages of chromatography with those of electrophoresis in one unit operation.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
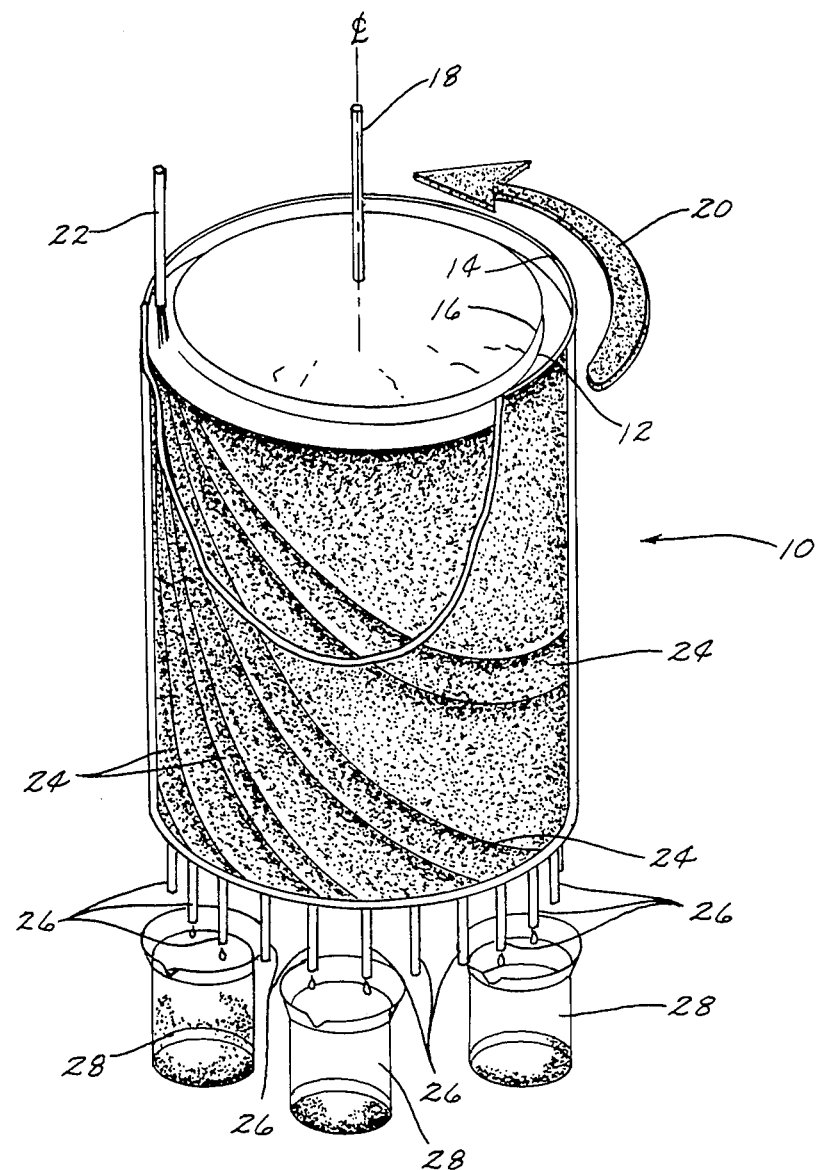
FIG. 1 is a simplified perspective view of the separation apparatus of the present invention illustrating the helical product paths of a number of products in a multi-component mixture, each product path having a stationary product collection point at a distinct angular coordinate at the bottom of the column.

Referring now to the drawings, wherein like reference numerals designate identical or corresponding parts throughout the several views, FIG. 1 shows the separation apparatus or continuous rotating annular electrophoresis column of the present invention generally designated by the reference numeral (10). The separation apparatus (10) includes an annular chamber or column (12) defined by an outer cylinder (14) and an inner cylinder (16). The annular chamber (12) is disposed to rotate about its central axis (18) in the direction of directional arrow (20). A fixed or stationary feed nozzle (22) is disposed to feed a multi-component chemical mixture at the top of the chamber (12). Differential response to an electric field applied axially with respect to the chamber (12), together with the rotation of the chamber (12), causes the individual components to separate and form helical product paths (24). Each helical product path (24) has a characteristic stationary exit point at some angular coordinate at the bottom of the chamber (12). A plurality of fixed or stationary product collections tubes (26) are disposed below the bottom of the chamber (12) and the individual separated product streams are collected in vessels (28).

Figure 2:
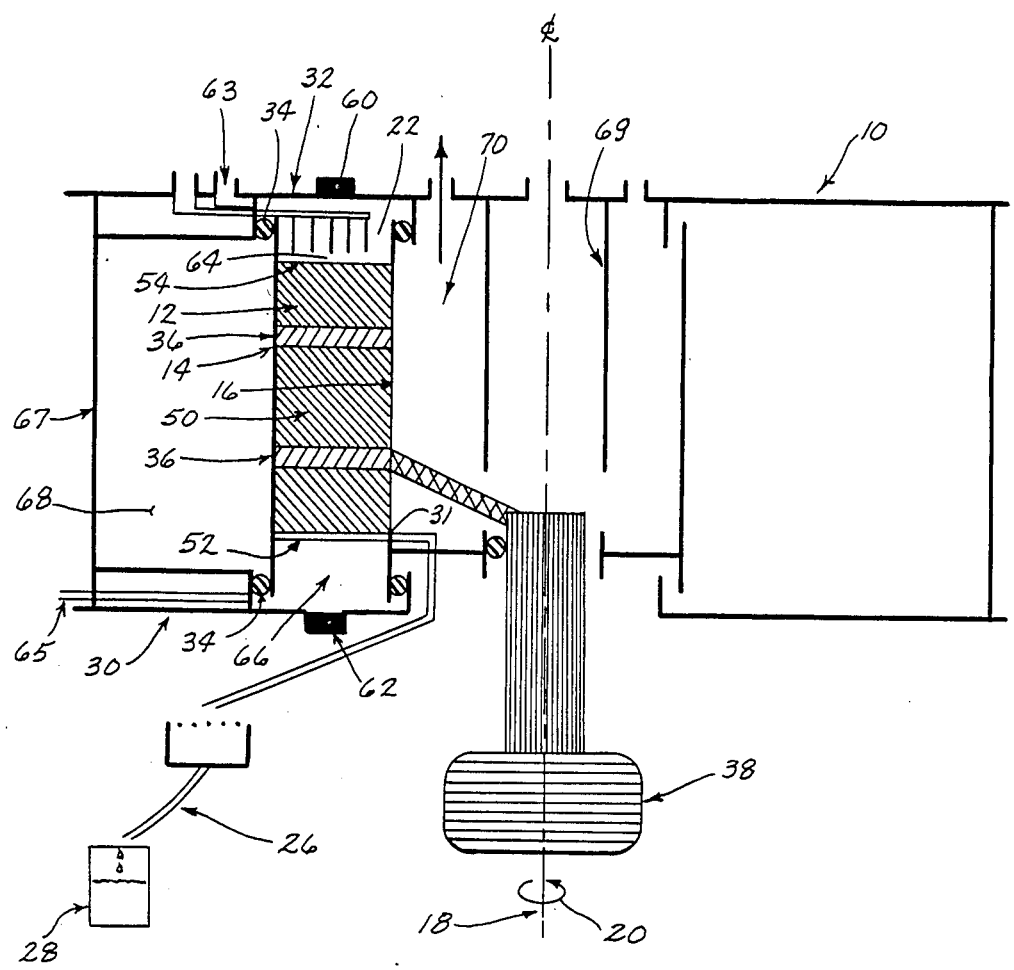
FIG. 2 is a sectional view of the continuous rotating annular electrophoresis column of the present invention, showing the electrodes positioned such that the electric field is applied to the column in the axial direction; the column is symmetric about its rotational axis although the structural detail of the right side is not illustrated.

Referring now to FIG. 2, one embodiment of the separation apparatus (10) is shown wherein the annular chamber (12) is disposed between base plate (30) and top plate (32) and is securely held therebetween by seals (34) and clamping screws (36). It is noted that the structural details shown in the left side of FIG. 2 are symmetric about the central axis (18). A rotational drive source (38) is operably attached to the inner cylinder (16) and acts to rotate the annular chamber (12) with respect to the central axis (18).

The first flush tube (63) supplies a continuous liquid stream to the first electrode compartment (64) in order to remove the gases caused by hydrolysis of water at the first electrode (60). The second flush tube (65) supplies a continuous liquid stream to the second electrode compartment (66) in order to remove the gases caused by hydrolysis of water at the second electrode (62).

In order to remove heat and to control the bed temperature, an outer stationary cooling jacket (67) is placed around the outer cylinder (14) to produce an external space (68) for cooling water circulation. A stationary cylindrical tube (69) placed about the central axis (18) forms an internal space (70) for additional cooling water circulation.

The annular chamber (12) receives an anti-convection packing (50) supported by a porous ring (52) capped by a layer of glass beads (54). The top or first electrode (60) and the bottom or second electrode (62) are connected to an appropriate direct current power supply (not shown). When a suitable electrical potential is applied, an axial potential gradient is established in the electrolyte disposed between the top and bottom electrodes (60) and (62). It is to be understood that the electrodes (60) and (62) could be a series of individual electrodes or a ring electrode disposed within the annular chamber (12).

In operation, a chemical mixture is introduced at the top of the rotating annular chamber (12) through the stationary feed nozzle (22). The mixture travels from the top or first axial end of the chamber (12) toward the bottom or second axial end thereof. Various driving forces, including gravity and pressurized gas, can be employed to cause the mixture to travel toward the second axial end of the chamber (12). The axial potential gradient established by the application of an electrical potential by the electrodes (60) and (62), together with the rotation of chamber (12), causes the individual components of the chemical mixture to separate into distinct helical product bands (24) each of which exits the second axial end of the chamber (12) at a given angular coordinate. The separated products exit the chamber (12) through an opening (31) in inner cylinder (16) which is in fluid communication with the stationary product collection tubes (26). Each product is then collected in a separate collection vessel (28). It is to be understood that the component of the mixture that is most strongly attracted to the bottom electrode (62) will have the shortest helical product path (24) and discharge at an angular coordinate closest to the angular coordinate of the fixed feed nozzle (22). The components less strongly attracted to the bottom electrode (62) will have longer helical product paths (24) and will discharge at angular coordinates further from the angular coordinate of the feed nozzle (22).

The rotation of the separation apparatus (10) results in several advantages including the stabilization of the flow in the carrier solution and the lengthening of the product migration path without increasing the length of the annular chamber (12). Also, application of the electrical field in the axial direction allows the use of a thin annulus width which improves heat transfer and allows good temperature control. Even greater temperature control can be achieved by providing for the jacketing of the annular chamber (12) wherein the jacket is fed by a constant temperature bath.

The continuous rotating annular electrophoresis column (10) can be hybridized to incorporate chromatography packing, thus combining the separation advantages of chromatography with those of electrophoresis in one unit operation. When in the electrochromatography mode, stationary or fixed elutant nozzles (not shown) are disposed at fixed positions around the annular chamber (12) to effect the desorbtion of the individual mixture components from the chromatography packing.

The feasibility of the apparatus of the present invention has been analyzed using a mathematical model. A summary of the predicted performance of units similar to the experimental unit of Vermeulen, et al., are presented in Table 1. A comparison of the column design of the present invention to Vermeulen's reveals that the continuous rotating annular electrophorosis unit has greater separations, a lower temperature rise, and requires less power to operate and therefore has lower operating costs. The lower temperature rise is extremely significant since the maximum allowable temperature rise in the separations of many biochemically active compounds is approximately 5°–10° C.

TABLE 1

Representative Results of the Continuous Rotating Electrophoresis Column

|  | A | B | C | D | Vermeulen's Design |
|---|---|---|---|---|---|
| Column Dimensions | | | | | |
| Inner Radius (cm) | 25.0 | 30.0 | 30.0 | 30.0 | 1.25 |
| Outer Radius (cm) | 35.0 | 35.0 | 35.0 | 35.0 | 10.00 |
| Length (cm) | 26.5 | 49.0 | 49.0 | 49.0 | 122.00 |
| Volume (cm$^3$) | $5.0 \times 10^4$ | $5.0 \times 10^4$ | $5.0 \times 10^4$ | $5.0 \times 10^4$ | $3.77 \times 10^4$ |

TABLE 1-continued

Representative Results of the
Continuous Rotating Electrophoresis Column

|  | A | B | C | D | Vermeulen's Design |
|---|---|---|---|---|---|
| Power (watts) | 175 | 350 | 525 | 700 | 712 |
| Residence Time (sec) | 7200 | 7200 | 7200 | 7200 | 7200 |
| Bed Voltage (volts) | 18.1 | 47.2 | 57.8 | 66 | 16 |
| Separation (cm) | 4.3 | 3.3 | 4.0 | 4.7 | 2.3 |
| Peak Temperature Rise (°C.) | 5.0 | 2.5 | 3.7 | 5.0 | 27.5 |

The continuous rotating annular electrophoresis separator of the present invention utilizes the principle of separation similar to the conventional electrophoresis and, therefore, will have many of its advantages—high resolution and product stability being the most important. In addition, the process is continuous and can be readily scaled up to increase system throughput for various industrial applications. The system design is such that temperature and material flow can be optimally controlled.

Thus, it can be seen that at least all of the stated objectives have been achieved.

Obviously, many modifications and variations of the present invention are possible in light of the above teachings. It is therefore to be understood that, within the scope of the appended claims, the invention may be practiced otherwise than as specifically described.

We claim:

1. In a separation apparatus including an annular chamber defined by sidewalls of an outer cylinder and an inner cylinder, said annular chamber having a first axial end disposed to receive a feed stream of a multi-component chemical mixture and a second axial end disposed to discharge separated components therefrom, means for continuously feeding said chemical mixture at the first axial end of the annular chamber, means for forcing said separated components toward the second axial end of the annular chamber, means for rotating the annular chamber with respect to the feeding means, and means for continuously discharging a plurality of separated components, each component being discharged from a distinct angular section of said second axial end, the improvement comprising:

a first electrode disposed at the first axial end of said annular chamber;

a first electrode compartment formed between said first electrode and said annular chamber;

a first flush tube disposed in fluid communication with said first electrode compartment thereby allowing the supply of a continuous liquid stream to said first electrode compartment to continuously remove the gases generated by the hydrolysis of water at said first electrode;

a second electrode disposed at the second axial end of said annular chamber;

a second electrode compartment formed between said second electrode and said annular chamber;

a second flush tube disposed in fluid communication with said second electrode compartment thereby allowing the supply of a continuous liquid stream to said second electrode compartment to continuously remove the gases generated by the hydrolysis of water at said second electrode; and means for applying an electrical potential between said first electrode and said second electrode, whereby an electrical potential gradient is established in an axial direction within said annular chamber.

2. The separation apparatus of claim 1 wherein said means for applying an electrical potential is a direct current power supply.

3. The separation apparatus of claim 1 wherein said chemical mixture feeding means includes a stationary feed nozzle disposed within said annular chamber.

4. The separation apparatus of claim 3 wherein said second axial end is disposed in fluid communication with a plurality of product collection tubes.

5. The separation apparatus of claim 1 wherein said chemical mixture forcing means includes gravitational force.

6. The separation apparatus of claim 1 wherein said chemical mixture forcing means includes pressurized gas.

7. The separation apparatus of claim 1 wherein said second axial end is disposed in fluid communication with a plurality of product collection tubes.

8. The separation apparatus of claim 7 wherein said product collection tubes are stationary.

9. The separation apparatus of claim 8 wherein said product collection tubes are stationary.

10. The separation apparatus of claim 9 wherein said stationary product collection tubes are disposed about the second axial end of said annular chamber in a plurality of distinct angular coordinates with respect to said stationary feed nozzle.

11. The separation apparatus of claim 1 further including an anti-convection packing disposed within said annular chamber.

12. The separation apparatus of claim 1 further including a chromatography packing disposed within said annular chamber.

13. The separation apparatus of claim 1 wherein said first electrode is an electrode ring disposed within said annular chamber.

14. The separation apparatus of claim 1 wherein said second electrode is an electrode ring disposed within said annular chamber.

15. The separation apparatus of claim 1 further including:

a stationary outer cooling jacket disposed radially outward from said outer cylinder; and a stationary cooling tube disposed radially inward from said inner cylinder, whereby heat is continuously removed from both sides of said annular chamber.

16. A process for separating individual components from a feed stream of a multi-component chemical mixture in a separation apparatus including an annular chamber defined by sidewalls of an outer cylinder and an inner cylinder, said annular chamber having a first axial end disposed to receive a feed stream of a multi-component chemical mixture and a second axial end disposed to discharge separated components therefrom, a first electrode disposed at the first axial end of said annular chamber and a second electrode disposed at the second axial end of said annular chamber, a feed nozzle disposed at the first axial end, and means for rotating the annular chamber with respect to the feed nozzle, said process including the steps of:

rotating said annular chamber with respect to said feed nozzle;

continuously feeding said chemical mixture through said feed nozzle into the first axial end of said chamber;

continuously applying an electrical potential between said first electrode and said second electrode thereby causing the separation of said chemical mixture into a number of individual separated components;

continuously forcing said separated components toward the second axial end of said annular chamber wherein each separated component flows through said chamber in a distinct helical path which terminates at a distinct angular section of said second axial end; and continuously collecting each separated component at a predetermined distinct angular section of said second axial end.

* * * * *